United States Patent
Barr et al.

(10) Patent No.: US 10,183,968 B2
(45) Date of Patent: Jan. 22, 2019

(54) METHODS OF PREPARING LYOPHILIZED SPHERICAL-SHAPED PELLETS OF BIOLOGICAL MATERIALS

(71) Applicant: Merck Sharp & Dohme Corp., Rahway, NJ (US)

(72) Inventors: Colleen Barr, Pennsburg, PA (US); Akhilesh Bhambhani, Doylestown, PA (US); Robert Evans, Souderton, PA (US); Lynne Isopi, Sellersville, PA (US); David Krah, Lansdale, PA (US); Jennifer Kriss, Blue Bell, PA (US); Jessica Sinacola, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 765 days.

(21) Appl. No.: 14/355,405

(22) PCT Filed: Oct. 26, 2012

(86) PCT No.: PCT/US2012/062246
§ 371 (c)(1),
(2) Date: Apr. 30, 2014

(87) PCT Pub. No.: WO2013/066769
PCT Pub. Date: May 10, 2013

(65) Prior Publication Data
US 2014/0294872 A1 Oct. 2, 2014

Related U.S. Application Data

(60) Provisional application No. 61/553,629, filed on Oct. 31, 2011.

(51) Int. Cl.
*F26B 5/06* (2006.01)
*C07K 1/14* (2006.01)
(Continued)

(52) U.S. Cl.
CPC .......... *C07K 1/14* (2013.01); *A61K 39/39591* (2013.01); *C07K 14/7151* (2013.01);
(Continued)

(58) Field of Classification Search
CPC ............... F26B 5/04; F26B 5/06; F26B 5/065
(Continued)

(56) References Cited

U.S. PATENT DOCUMENTS 3,655,838 A    4/1972  Price et al.
4,213,949 A *  7/1980  Mahler .................... B01J 20/16
                                                      106/409
(Continued)

FOREIGN PATENT DOCUMENTS

EP    0799613 B1    7/2001
WO    2002061351 A1    8/2002
(Continued)

OTHER PUBLICATIONS

European Search Report, European Search Report, European Search Report, dated Jun. 15, 2015, 6 pages, European Search Report.
(Continued)

*Primary Examiner* — John McCormack
(74) *Attorney, Agent, or Firm* — Letitia Walker; Laura M. Ginkel

(57) ABSTRACT

Methods for preparing lyophilized pellets of biological materials are described. The pellets have a substantially spherical shape and are prepared by freezing droplets of a liquid composition of a desired biological material on a flat, solid surface, in particular, a surface that does not have any cavities, followed by lyophilizing the frozen droplets. These methods are useful for preparing lyophilized pellets having a high concentration of a desired biological material, in
(Continued)

particular a therapeutic protein or vaccine, and which have a faster reconstitution time than lyophilized powder cakes prepared in vials.

20 Claims, 5 Drawing Sheets

(51) Int. Cl.
*A61K 39/395* (2006.01)
*C07K 16/00* (2006.01)
*C07K 14/715* (2006.01)

(52) U.S. Cl.
CPC ............... *C07K 16/00* (2013.01); *F26B 5/06* (2013.01); *C07K 2317/10* (2013.01); *C07K 2317/94* (2013.01); *C07K 2319/30* (2013.01)

(58) Field of Classification Search
USPC ................ 34/297, 284–287, 289, 290
See application file for complete search history.

(56) References Cited

U.S. PATENT DOCUMENTS

| | | | | |
|---|---|---|---|---|
| 4,707,998 | A * | 11/1987 | Linner | B01D 8/00 118/50.1 |
| 5,017,383 | A * | 5/1991 | Ozawa | A61K 9/5089 424/475 |
| 6,828,416 | B1 * | 12/2004 | Lal | C07K 14/445 424/139.1 |
| 7,074,401 | B2 | 7/2006 | Gurewich et al. | |
| 7,820,798 | B2 * | 10/2010 | Yu | A61K 51/08 435/326 |
| 9,415,392 | B2 * | 8/2016 | Ismagilov | B01L 3/502738 |
| 2002/0052317 | A1 * | 5/2002 | Itri | A61K 38/1816 424/85.4 |
| 2007/0259348 | A1 * | 11/2007 | Phadke | C12Q 1/6806 435/6.12 |
| 2008/0187578 | A1 * | 8/2008 | Lee | A61K 9/0078 424/450 |
| 2009/0133410 | A1 | 5/2009 | Thorne et al. | |
| 2009/0142771 | A1 | 6/2009 | Breidenthal et al. | |
| 2010/0247506 | A1 | 9/2010 | Johnstone et al. | |
| 2011/0155620 | A1 * | 6/2011 | Kuu | A61K 9/19 206/524.1 |

FOREIGN PATENT DOCUMENTS

| | | |
|---|---|---|
| WO | 2006008006 A1 | 1/2006 |
| WO | WO2006119280 A2 | 11/2006 |
| WO | 2009068545 A1 | 6/2009 |
| WO | 2010104526 A1 | 9/2010 |
| WO | 2010125087 A1 | 11/2010 |
| WO | 2009092703 A1 | 6/2011 |
| WO | WO2011124667 | 10/2011 |
| WO | WO2013066769 A1 | 5/2013 |

OTHER PUBLICATIONS

Canadian Office Action, Canadian Application No. 2,853,816, entitled "Methods of Preparing Lyophilized Spherical-Shaped Pellets of Biological Material", dated Oct. 15, 2018, 1-5.

* cited by examiner

METHODS OF PREPARING LYOPHILIZED SPHERICAL-SHAPED PELLETS OF BIOLOGICAL MATERIALS

CROSS REFERENCE TO RELATED APPLICATIONS

This application is the National Stage of International Application No. PCT/US2012/062246 filed on Oct. 26, 2012, which claims the benefit under 35 U.S.C. 119(e) of U.S. Provisional Application No. 61/553,629, filed Oct. 31, 2011.

BACKGROUND OF THE INVENTION (1) Field of the Invention

The present invention relates to methods for preparing lyophilized pellets of biological materials such as proteins, in particular to methods of preparing lyophilized pellets of biological materials that are spherical in shape and have fast reconstitution times.

(2) Description of Related Art

Biological materials such as cells, proteins and vaccines are frequently preserved by lyophilizing aliquots of a liquid composition containing the biological material. The lyophilization process involves freezing a liquid sample which is then subjected to a vacuum so that the ice in the frozen sample directly changes to water vapour or sublimes. After the removal of ice, the sample temperature is gradually increased (while still under vacuum) and water is desorbed from the remaining non-ice phase of the sample.

Lyophilized cakes of a biological material are prepared by aliquoting into a glass container a desired amount of the biological material, which is typically present in a buffered solution with appropriate stabilizers (i.e., a "formulation") and then subjecting the glass container containing the biological material to steps of cooling, freezing, annealing, primary drying and secondary drying. The glass container containing the dried biological material is typically stored for long periods of time at room temperature or under refrigerated conditions. The dried formulation containing the biological material is typically reconstituted by adding a liquid, usually water, to the glass container. Glass containers used for lyophilizing biological materials intended for use as therapeutics and vaccines typically have included glass vials and dual chamber injection devices, in which one chamber contains the lyophilized cake and the other chamber contains the reconstituting liquid.

Methods of lyophilizing biological materials in the form of spherically shaped pellets, i.e., beads, have also been described. In these methods, individual samples of the biological material are frozen and dried prior to placing a desired number of the dried samples into a storage container such as a glass vial. Historically, these methods relied on either (a) dispensing an aliquot of a liquid composition containing the desired amount of a biological material into a container of a cryogen such as liquid nitrogen, which results in direct contact of the biological material with the cryogen and/or (b) dispensing an aliquot of a liquid composition containing the biological material into a cavity present on a chilled solid plate, where the cavity contains the aliquot until it is frozen. It should also be noted that the use of plates with machined cavities often requires use of an automated system for detachment of the pellets from the cavity wall. Furthermore, reliance on a cavity to contain the liquid aliquot results in a volume restriction on the size of the aliquot and resulting pellet. Another approach, which is referred to as the die and punch method and uses a closed mould and compressive force to obtain a frozen pellet, suffers from a complex assembly design, leakage of fluid formation from the cavity and sticking of pellet to either the die or the punch.

BRIEF SUMMARY OF THE INVENTION

The present invention relates to a method for preparing dried pellets (<5% moisture) of a fluid formulation of a biological material, to the dried pellets prepared using the method, and to uses thereof.

The method comprises dispensing at least one liquid droplet having a substantially spherical shape onto a solid and flat surface (i.e., lacking any sample wells or cavity), freezing the droplet on the surface without contacting the droplet with a cryogenic substance and lyophilizing the frozen droplet to produce a dried pellet that is substantially spherical in shape. The method may be used in a high throughput mode to prepare multiple dried pellets by simultaneously dispensing the desired number of droplets onto the solid, flat surface, freezing the droplets and lyophilizing the frozen droplets. It has been surprisingly found that pellets prepared by the method of the invention from a liquid formulation having a high concentration of a biological material such as a protein therapeutic may be combined into a set of dried pellets that has a faster reconstituted time than a single lyophilized cake prepared by freezing and lyophilizing the same volume of the liquid formulation in a glass container.

In one embodiment of the invention, the solid, flat surface is the top surface of a metal plate which comprises a bottom surface that is in physical contact with a heat sink adapted to maintain the top surface of the metal plate at a temperature of −90° C. or below. Because the top surface of the metal plate is well below the freezing point of the liquid formulation, the droplet freezes essentially instantaneously with the bottom surface of the droplet touching the top surface of the metal plate.

In another embodiment, the solid, flat surface is hydrophobic and comprises the top surface of a thin film that is maintained above 0° C. during the dispensing step. The dispensed droplet is frozen by cooling the thin film to a temperature below the freezing temperature of the formulation.

The present invention also relates to a container comprising at least one dried pellet that is substantially spherical in shape that is prepared using either of the above metal plate or hydrophobic, thin film embodiments. In one embodiment, the biological material is a protein therapeutic and the container comprises a set of dried pellets.

In yet another aspect, the invention includes a container comprising at least two dried pellets that are substantially spherical in shape, wherein one of the two dried pellets comprises a first biological material and the other dried pellet comprises a second biological material that is different than the first biological material, wherein each of the dried pellets in the container is prepared by (a) dispensing a droplet having a substantially spherical shape onto a metal plate, wherein the metal plate comprises a solid and flat surface that is maintained at a temperature of −90° C. or lower such that the dispensed droplet freezes as it contacts the surface, (b) lyophilizing the frozen droplet to produce the dried pellet having a substantially spherical shape, and (c) placing the dried pellet into the container. In one embodiment, the first and second biological materials comprise different components of a multi-component vaccine.

DETAILED DESCRIPTION OF THE INVENTION

Figure 1:
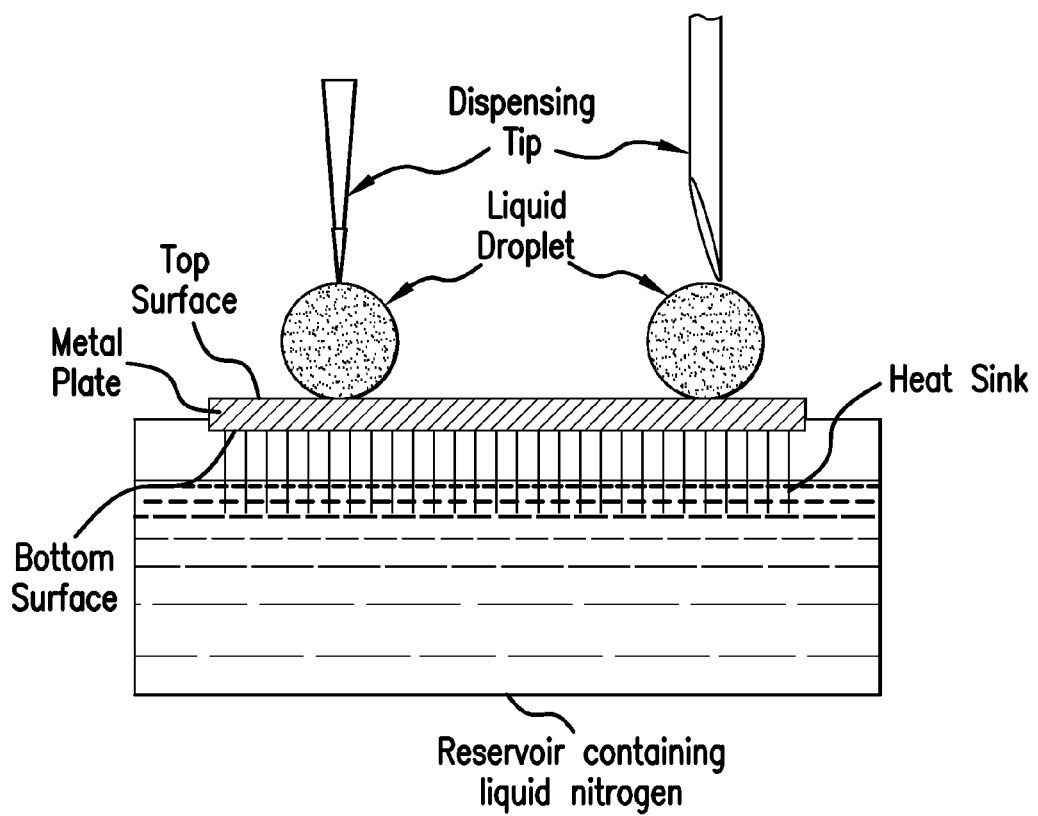
FIG. 1 illustrates the freezing of a dispensed liquid droplet according to one embodiment of the invention, in which the dispensed droplet is transiently bound on either side by the open end of the dispensing tip and the tope surface of a metal plate that has a bottom surface in contact with a heat sink comprising a plurality of metal fins immersed in liquid nitrogen contained in a reservoir.
Figure 2:
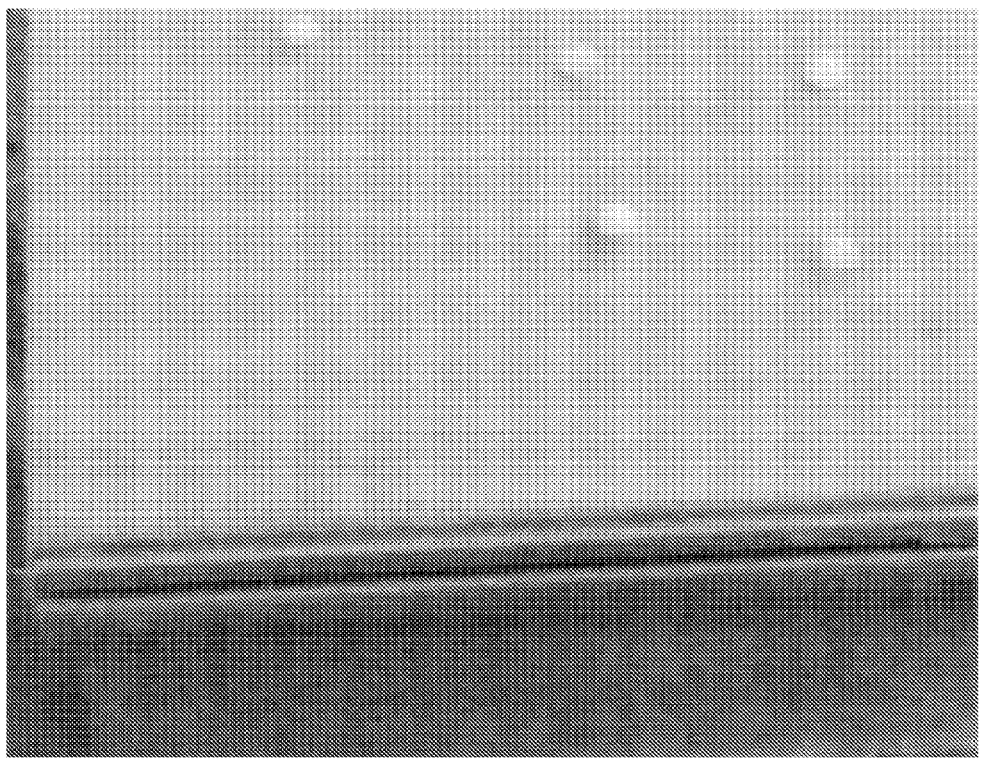
FIG. 2 is a photograph of frozen droplets prepared on a metal plate as illustrated in FIG. 1, wherein the top surface of the metal plate was maintained at a temperature of −190° C.
Figure 3:
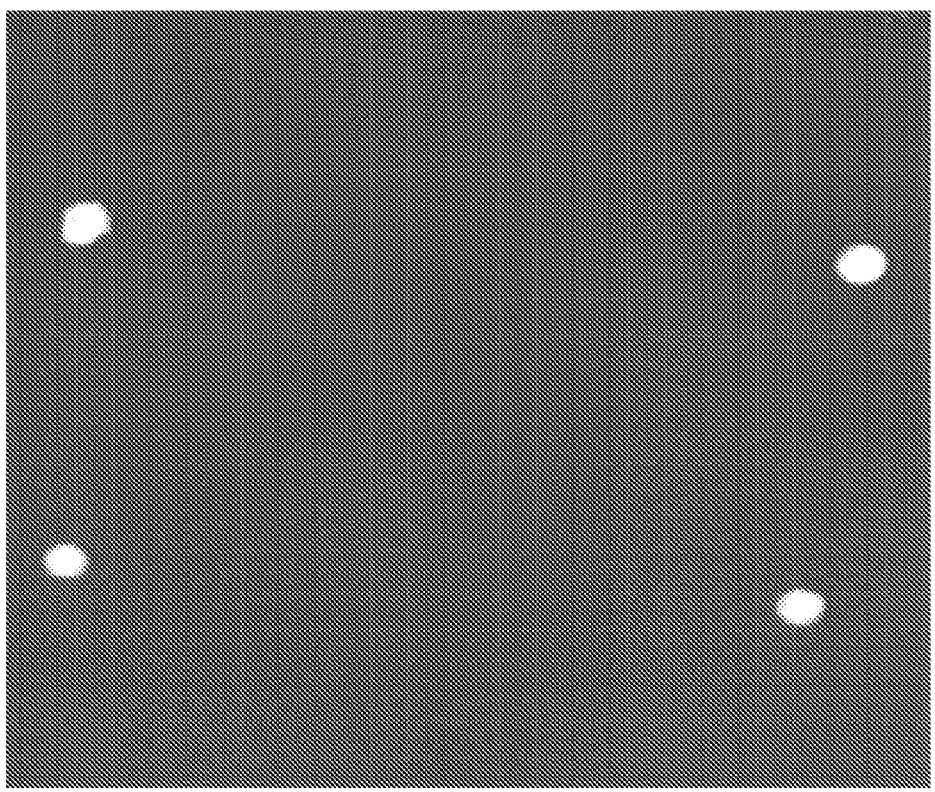
FIG. 3 is a photograph of dried pellets on a hydrophobic film prepared according to one embodiment of the invention.

The method of making dried pellets of a biological material according to the invention comprises loading an aliquot of a liquid composition (such as a liquid protein formulation) comprising the biological material into a dispensing tip and dispensing the aliquot onto a solid, flat surface in such a way that the droplet remains intact while being dispensed. The term "solid, flat surface" means that there are no cavities or wells. Dispensing tips useful in the present invention include those with a round open end, and a pointed open end, as shown in FIG. 1. Multiple dried pellets may be prepared simultaneously by loading simultaneously the desired number of aliquots of the liquid composition into a multichannel pipettor.

In one embodiment, the solid, flat surface is the top surface of a metal plate and is maintained at a temperature of −90° C. or lower. In some embodiments of the invention, the temperature of the metal plate is −150° C. or lower, or −180° C. or lower. In other embodiments, the temperature of the plate is within a range of about −90° C. to about −130° C., about −110° C. to about −150° C., about −150° C. to about −195° C. or −180° C. to about −196° C. The metal plate comprises a conductive, inert metal such as gold, silver, stainless steel, aluminum or copper. In a preferred embodiment, the metal plate is comprised of aluminum. In another preferred embodiment, the plate is stainless steel. In some embodiments, the metal plate is rectangular in shape, and in one preferred embodiment, the dimensions of the rectangular plate are 10 inches long×7 inches wide×0.4 inches thick.

The cold temperature of the metal plate is maintained by placing the bottom surface of the metal plate in physical contact with a heat sink. In one preferred embodiment, the heat sink comprises a plurality of fins composed of a temperature conductive metal. In some embodiments, the fins are spaced about 0.25 inches apart along the bottom surface of the metal plate, with each fin having a length of at least about one inch. For a 10 inch×7 inch plate, the heat sink preferably comprises thirty, one inch long fins.

The fins may be physically connected to the bottom of the metal plate using any of a multitude of approaches well-known in the art, for example, using metal screws, welding, gluing with a cryoglue. In such an embodiment, the term "bottom surface" means the surface of the plate that is physically connected to the plurality of fins. Alternatively, the metal plate and heat sink may be fabricated from a single metal block and in such a case, the skilled artisan will understand that the bottom surface of the metal plate and heat sink form part of the same functional feature and thereby in physical contact with each other.

An example of a heat sink that is fabricated from a single metal block, and useful in the present invention, is illustrated in FIG. 1. This plate comprises a plurality of metal fins having one end in physical contact with the bottom surface of the metal plate, which rests on top of a metal reservoir containing a liquid cryogen such as liquid nitrogen. Other liquid cryogens that may be used in the heat sink include liquid propane, isopentane/hexane mixtures, argon and HFE-7100. The metal fins and reservoir are preferably made of the same conductive metal as used for the plate. Similar heat sinks may be purchased commercially, e.g., from M&M Metals, 1305 W Crosby Road, Carrollton, Tex.

In another embodiment, the solid, flat surface is hydrophobic and is maintained above 0° C. during the dispensing step, and preferably between 4° C. and 25° C. The hydrophobic surface may comprise a chemically inert plastic such as polytetrafluoroethylene (PTFE), polypropylene and the like. The hydrophobic surface may be bonded to a different material or simply comprise the top surface of a thin film made using the hydrophobic material (e.g., PTFE, polypropylene). To freeze the liquid droplet, the film containing the dispensed droplet is chilled to a temperature that is below the freezing point of the liquid composition comprising the biological material, and preferably to a temperature of about 5° C. to 25° C. below the freezing point.

It is important to maintain the liquid droplet intact during the dispensing step. When the droplet is dispensed onto a cold metal surface (i.e., −90° C. or lower), one way of accomplishing this is to dispense the droplet at a dispensing speed and at a distance between top surface and the bottom of the dispensing tip (the "gap distance") that prevents the droplet from freezing while any portion of the droplet is still in the tip, and maintains the dispensed droplet in simultaneous contact with the top surface of the metal plate and the bottom of the dispensing tip, for example as shown in FIG. 1. This allows the droplet to freeze from the bottom up as it contacts the cold metal surface.

The dispensing speed and gap distance will depend upon the volume of the liquid droplet, and the shape of the open end of the dispensing tip, and may be readily determined experimentally. For a 250 ul bead, for example, this speed could range from 0.2 second to 3.0 second. Similarly for 100 ul bead, for example, the dispensing speed could range from 0.1 second to 2 second. In the preferred embodiment, the dispensing speed is within the range of about 3 ml/min to about 75 ml/min, about 5 ml/min to about 75 ml/min, about 3 ml/min to about 60 ml/min, about 20 ml/min to about 75 ml/min, 20 ml/min to about 60 ml/min, respectively. A suitable dispensing speed for preparing 50 and 20 microliter droplets is 4.5 ml/min of a composition with low solute concentration (5%) and 9 ml/min for a composition with high solute (25%) concentration.

In an alternative embodiment, the gap distance (i.e., between the open end of the dispensing tip and the top surface) is high enough so that the dispensed drop is in contact only with the top surface of the cold metal plate. To maintain the intactness and spherical shape of the droplet, the temperature of the metal surface is maintained well below −150° C. to ensure instantaneous freezing of the liquid droplet as it touches the surface. The gap distance will depend on the volume of the dispensed aliquot, but is usually at least 1 cm.

When the liquid droplet is dispensed onto a hydrophobic surface, the droplet is typically maintained intact in a substantially spherical shape by choosing a volume for the aliquot that will remain intact as the droplet touches the surface.

In preferred embodiments, the dispensing tip or tips are connected to an automated dispensing unit capable of controlling the dispensing speed and the gap distance. Examples of automated dispensing units include the Biomek® FX Liquid Handling System and pipettors manufactured by Tecan.

In some embodiments, the method further comprises measuring the reconstitution time of the dried pellet. The term "reconstitution time" refers to the time that is required to completely dissolve a dried pellet, i.e., prepared according to the present invention, or a lyophilized cake to produce a reconstituted liquid formulation that is clear.

After the pellets are frozen, they are placed in a lyophilization chamber and lyophilized. The steps of a typical lyophilization cycle useful in the present invention include loading, annealing, freezing, and one or more drying steps. In some embodiments, the drying step(s) is performed above 0° C. A preferred lyophilization cycle will keep the drying droplet below the collapse temperature and produce a dried pellet of substantially the same shape and size of the frozen droplet, and having a moisture content of about 0.1% to about 10%, about 0.1% to about 6%, about 0.1% to about 3% or 0.5% to about 5%. Examples of lyophilization cycles are shown below.

Lyophilization Parameters I
Load: −45° C./0.5/15 min
Annealing: −20° C./0.5/60 min
Freezing: −45° C./0.5/75 min
Primary Drying: 30° C./0.65/1350/30 mTorr
Secondary Drying: 30° C./0.65/270 min/255 mTorr
Lyophilization Parameters II
Load: −45° C./0.5/15 min
Annealing: −20° C./0.5/60 min
Freezing: −45° C./0.5/75 min
Primary Drying: 15° C./0.65/1590 minr/30 mTorr
Secondary Drying: 30° C./0.65/300 min/255 mTorr
Lyophilization Parameters III
Load: −45° C./0.5/15 min
Annealing: −20° C./0.5/60 min
Freezing: −45° C./0.5/75 min
Primary Drying: 15° C./0.65/28 hr/30 mTorr
Secondary Drying: 15° C./0.65/5 hr/210 mTorr After completion of lyophilization, the dried pellets may be placed in a container for bulk storage, or aliquoted into desired end-use container. Bulk storage containers include, e.g., plastic trays, metal trays, bottles, foil bags, and the like. The desired end-use container may be configured to receive a liquid for reconstitution directly in the container, e.g., a vial, or commercially available dual chamber containers, such as a dual-chamber cartridge pen device, dual chamber foil packet, a plastic tube with two or more chambers and designed to readily mix two or more components immediately before administration of the therapeutic or vaccine in the pellet. Alternatively, the end-use container may be adapted to allow removal of a desired number of pellets, e.g., such as a bead dispenser, and the removed pellets are then reconstituted with liquid in a separate container.

The method of the present invention may be utilized to prepare dried pellets of a variety of biological materials, including therapeutic proteins such as cytokines, enzymes and antibodies, as well as antigenic substances used in vaccines, such as peptides and proteins. The biological material is typically in a liquid composition that also contains one or more components that confer stability on the biological material during storage of the liquid formulation, as well as during and after the freezing and lyophilization steps. This liquid composition is also referred to herein as a "liquid formulation," "pharmaceutical composition," "vaccine composition," and "vaccine formulation". Additional components that may be included as appropriate include pharmaceutically acceptable excipients, additives, diluents, buffers, sugars, amino acids (such as glycine, glutamine, asparagine, arginine or lysine), chelating agents, surfactants, polyols, bulking agents, stabilizers, cryoprotectants, lyoprotectants, solubilizers, emulsifiers, salts, adjuvants, tonicity enhancing agents (such as alkali metal halides, preferably sodium or potassium chloride, mannitol, sorbitol), delivery vehicles and anti-microbial preservatives. Acceptable formulation components for pharmaceutical preparations are nontoxic to recipients at the dosages and concentrations employed.

In some embodiments, the total excipient concentration in the composition used to prepare the pellets comprises 50% or less on a weight by weight basis (w/w) of excicipients that have plasticizing effects, such as glycerol and sorbitol. Such exicipients result in dried pellets that are fragile or spongy, which are undesirable characteristics for subsequent processing operations. The skilled artisan can readily identify other exicipients that have plasticizing effects. In other embodiments, the pellets are prepared from compositions having at least 5% solute concentration w/w.

The inclusion of cationic polymers, such as polybrene, that are typically used in cell culture for manufacturing virus antigens and proteins, should be avoided as the inventors herein have surprisingly discovered that even small amounts (e.g., a 5 microgram concentration) of polybrene in the composition results in pellets that fracture during or after freezing.

The method of the present invention is particularly useful for preparing dried pellets from liquid formulations having a high concentration of a therapeutic antibody, e.g. 50 mg/ml or more, and that has a reconstitution time of less than 3 minutes, preferably less than 2 min. The dried pellet is typically stable for at least 1 month at room temperature (e.g., 25° C.), and preferably at least 6 months at room temperature (e.g., 25° C.). Upon reconstitution, the formulation is suitable for parenteral administration such as intravenous, intramuscular, intraperitoneal or subcutaneous injection.

The method of the present invention is also particularly useful for preparing dried spherical shaped pellets from compositions having a high solute concentration, e.g., concentrations above 20%. Such compositions may have high concentrations of sugars and other stabilizers, e.g., sucrose, trehalose, sucrose/trehalose mixtures, mannitol, dextrose, dextran and mixtures of such sugars. Compositions with a high solute concentration are not typically employed in products lyophilized in vials due to difficulty in achieving a satisfactory dried product with reasonable lyophilization cycles. However, as demonstrated below, frozen spherical shaped droplets using the method described herein may be prepared from different types of compositions, including compositions with a low or high solute concentration, and dried using shorter lyophilization cycles than if done in vials.

The dried pellets prepared by the method of the present invention can be easily integrated into a variety of dosage sizes by choosing the volume of the droplet used to prepare each pellet and the number of pellets added to a single or multiple dosage container or delivery device. Also, the invention readily enables the preparation of combination therapeutic or immunogenic products, in which dried pellets comprising one biological material are combined in a single container with dried pellets comprising a different biological material. For example, pellets prepared from different antigen compositions, such as measles, mumps, rubella, and varicella, may be combined in a single container to obtain a multi-component vaccine. This allows the different antigens to remain separate until reconstitution, which can increase shelf-life of the vaccine. Similarly, combination products may contain separate antigen-comprising pellets and adjuvant-comprising pellets. Another example would be a combination of pellets comprising a protein with pellets comprising a peptide.

EXAMPLES

In all of the examples below, frozen droplets of the test compositions were prepared using a metal plate/heat sink apparatus very similar to that shown in FIG. 1. The metal plate/heat sink was made of aluminum as large as 10 inches long×7 inches wide×0.4 inches thick and had a flat top surface and a bottom surface with thirty, 1 inch long fins spaced perpendicularly thereto about 0.25 inches apart. The fins were submerged in liquid nitrogen contained in an aluminum reservoir or a styrofoam reservoir that was big enough to hold the metal plate/heat sink.

Example 1. Preparation of Dried Pellets Comprising an IgG1 Antibody

This method of the present invention was exemplified using an IgG antibody at 100 mg/ml. A liquid antibody composition comprising the antibody at 100 mg/ml was prepared and frozen droplets of this composition were obtained by pipetting various size aliquots on a solid, flat metal plate having a surface temperature ≤−100° C. Pellets of four different sizes were obtained by aliquoting 20-22 ul, 25 ul, 50 ul and 100 ul of the liquid antibody composition on the cold plate. The frozen droplets were lyophilized and then placed in glass vials for storage. As a control, various volumes (0.25 ml, 0.5 ml, 1 ml and 1.5 ml) of the same liquid antibody composition were placed into 3 ml glass vials and lyophilized. The times required to reconstitute the dried pellets as compared to the same quantity of antibody in dried pellets was measured using a stop watch staring with the addition of a reconstitution volume of SWFI (Sterile Water for Injection) and ending with complete dissolution of all of the dried pellets or lyophilized cake in a glass vial (as determined by visual inspection). The reconstitution times are shown for vials containing 5 pellets of 100 ul each or 10 pellets of 50 ul each. For comparison purposes, reconstitution time of lyophilized cake at 0.5 ml (pre-lyophilization) fill was also measured. The results are shown in Table 1 below.

TABLE 1

Reconstitution times.

| | Configuration | Recon volume (ul) | Time |
|---|---|---|---|
| 1 | 0.25 ml/vial | 0.25 ml | 3 min 30 s |
| 2 | 0.5 ml/vial | 0.5 ml | 4 min |
| 3 | 1.0 ml/vial | 1 ml | 27 min |
| 4 | 1.5 ml/vial | 1.5 ml | 16 min |
| 5 | 10 of 20 ul spheres/vial | 0.2 ml | <1 min |
| 6 | 10 of 20 ul spheres/vial | 0.2 ml | <1 min |
| 7 | 10 of 25 ul spheres/vial | 0.25 ml | <1 min |
| 8 | 10 of 25 ul spheres/vial | 0.25 ml | <1 min |
| 9 | 10 of 50 ul spheres/vial | 0.5 ml | <1 min |
| 10 | 20 of 50 ul spheres/vial | 1 ml | <1 min |
| 11 | 20 of 50 ul spheres/vial | 1 ml | <1 min |
| 12 | 10 of 100 ul spheres/vial | 1 ml | <1 min |

A configuration listed as 10 of 20 μl spheres/vial means the vial contained 10 dried pellets prepared using 20 μl antibody composition. Similarly, a configuration listed as 20 of 50 μl spheres/vial means the vial contained 20 dried pellets prepared using 50 μl antibody composition. The lyophilized cakes/pellets obtained were also characterized by visual appearance, moisture content analysis and absorbance measurements.

Figure 4:
FIG. 4 is a photograph of 3 cc vials containing 50 mg of a lyophilized antibody formulation that was prepared from a 100 mg/ml liquid antibody formulation with the left vial containing a lyophilized cake prepared by dispensing and lyophilizing 0.5 ml of the liquid antibody formulation in the vial; the middle vial containing 10 dried pellets, with each pellet prepared by dispensing 50 ul of the liquid antibody formulation onto a cold metal plate; and the right vial containing 5 pellets, with each pellet prepared by dispensing 100 ul of the liquid antibody formulation onto a cold metal plate.
Figure 5:
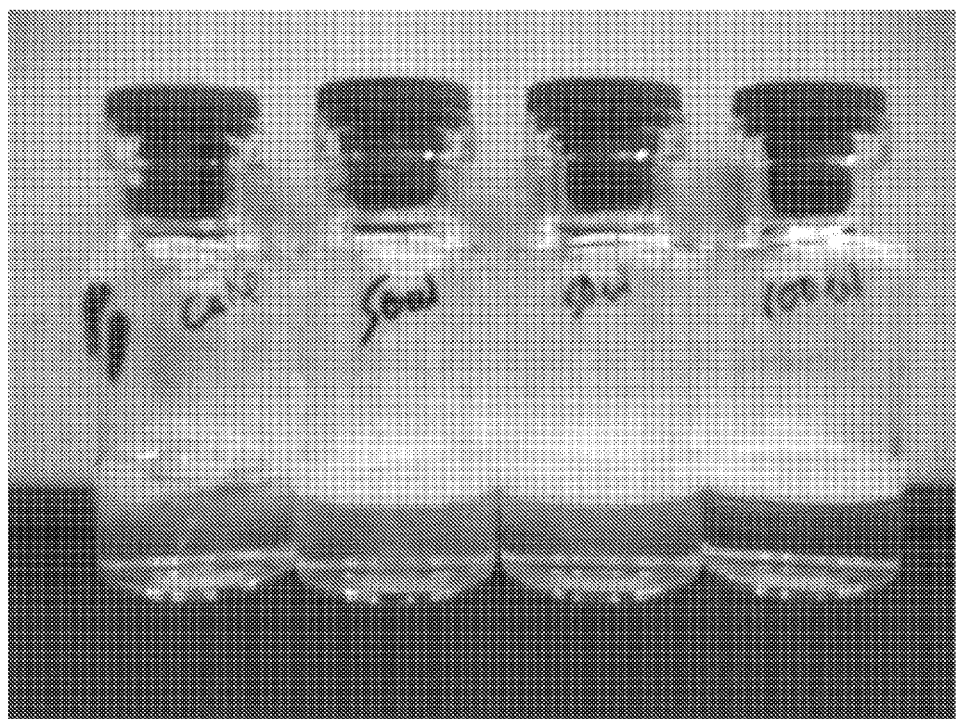
FIG. 5 is a photograph taken 10 min after adding water to four vials containing equivalent amounts (50 mg) of a lyophilized antibody formulation prepared from a 100 mg/ml liquid antibody formulation in which the left vial contained a lyophilized cake prepared by dispensing and lyophilizing 0.5 ml of the liquid antibody formulation in the vial; the middle two vials contained 10 dried pellets, with each pellet prepared by dispensing 50 ul of the liquid antibody formulation onto a cold metal plate; and the right vial containing 5 pellets, with each pellet prepared by dispensing 100 ul of the liquid antibody formulation onto a cold metal plate.

As seen in Table 1, the dried pellets were completely dissolved in significantly less time than lyophilized cakes containing an equivalent amount of antibody. The faster reconstitution times of the dried pellet configuration versus the lyophilized cake configuration is also apparent from the photographs shown in FIGS. 4A and 4B.

Example 2. Preparation of Dried Pellets Comprising a Fusion Protein

The method of the present invention was applied to a liquid composition comprising 25 mg/ml of a TNFRII-Fc fusion protein, which was produced by expression of a recombinant DNA that has a coding sequence for soluble human Tissue necrosis factor receptor 2 fused to a coding sequence for the Fc component on human IgG1. The composition also contained 40 mg/ml mannitol, 10 mg/ml sucrose, and 1.2 mg/ml tromethamine in sterile water, pH 7.4.

Droplets of 50 μL each were dispensed using the start/stop function of a KDS Legato™ 200 pump assembled with a 5 ml syringe and 18G1 needle onto the solid, flat top surface of the metal plate/heat sink apparatus having a surface temperature of ~−190° C. The frozen droplets were lyophilized in a monolayer format using a lyophilization cycle similar to the Lyophilization Parameters II described above. The lyophilized pellets and cakes were stored under refrigeration (2-8° C.) for two weeks and then evaluated for solubility and other characteristics relating to antibody stability.

To assess the effect of this process on stability of the fusion protein, the dried pellets were reconstituted in 1 ml sterile water, 0.9% benzyl alcohol and thermal unfolding of the fusion protein was measured by Differential Scanning calorimetry (DSC) and Circular Dichroism (CD) spectroscopy. An unlyophilized sample of the same liquid composition was used as a control. CD melts were performed on samples in an auto Peltier 6 cell changer with 1 cm quartz cuvette at a wavelength of 217 nm with a ramp rate of 1 C/min in a temperature range of 20-95° C.

The DSC results indicated that onset temperature for unfolding and mid-point transition temperatures of the fusion protein in the reconstituted formulation was similar to those for the fusion protein in the starting liquid formulation (Tm1 around 77° C. and Tm2 around 88° C. for all the formulations tested). Similarly, the unfolding temperature determined by CD when the signal was measured at 217 nm during temperature ramp was not significantly different between the starting liquid and reconstituted samples (Tm around 65.5° C.).

What is claimed:

1. A method of preparing a lyophilized pellet of a biological material, comprising:
   providing a vessel which contains a liquid composition comprising the biological material;
   providing a metal plate which comprises a top surface that is solid and flat and does not contain a hydrophobic film and a bottom surface that is in physical contact with a heat sink adapted to maintain the top surface of the metal plate at a temperature of −90° C. or below;
   positioning a dispensing tip above the top surface of the metal plate, the dispensing tip having an open end configured to dispense liquid droplets and another end connected to the vessel, wherein there is a gap of at least 0.1 cm between the top surface of the metal plate and the open end of the dispensing tip;
   dispensing an aliquot of the liquid composition through the open end of the dispensing tip as a single droplet onto the top surface of the metal plate in a manner that maintains the droplet as a single droplet having a substantially spherical shape as it contacts and freezes on the top surface; and lyophilizing the frozen droplet to produce a dried pellet of substantially spherical shape.

2. The method of claim 1, wherein the dispensing is performed at a speed and at a gap distance that prevents freezing of any portion of the aliquot in the dispensing tip and maintains the droplet in simultaneous contact with the top surface of the metal plate and the open end of the dispensing tip until the droplet surface touching the plate is frozen.

3. The method of claim 2, wherein the dispensing speed is selected from the group consisting of: 3 ml/min to 75 ml/min; 5 ml/min to 75 ml/min; 3 ml/min to 60 ml/min, 20 ml/min to 75 ml/min; and 20 ml/min to 60 ml/min.

4. The method of claim 2, wherein the aliquot is 250 µl and the dispensing speed is between 5 ml/min to 75 ml/min, or wherein the aliquot is 100 µl and the dispensing speed is between 3 ml/min to 60 ml/min.

5. The method of claim 1, wherein the top surface temperature of the metal plate is below −150° C. and a gap distance between the open end of the dispensing tip and the top surface of the metal plate is between 0.1 cm and 0.5 cm or between 0.1 cm and 1 cm or between 0.1 cm and 0.75 cm.

6. The method of claim 5, wherein the surface temperature of the metal plate is between −180° C. and −196° C. or between −180° C. and −273° C.

7. The method of claim 1, wherein the heat sink comprises a plurality of metal fins having first and send ends and arranged perpendicularly to the metal plate, with the first end of each fin touching the bottom surface of the metal plate and the second end of each fin immersed in liquid nitrogen.

8. The method of claim 1, wherein the biological material is selected from the group consisting of a purified antibody at a concentration in the liquid composition of at least 50 mg/ml or 100 mg/ml; a vaccine, a fusion protein, a polypeptide, and a peptide.

9. The method of claim 1, wherein the liquid composition comprises a total solute concentration of at least 25 on a weight by weight basis.

10. The method of claim 1, further comprising measuring the reconstitution time of the lyophilized pellet.

11. A container containing at least one lyophilized pellet, wherein the lyophilized pellet is prepared by:
    providing a vessel which contains a liquid composition comprising a biological material;
    providing a metal plate which comprises a top surface that is solid and flat and does not contain a hydrophobic film and a bottom surface that is in physical contact with a heat sink adapted to maintain the top surface of the metal plate at a temperature of −90° C. or below;
    positioning a dispensing tip above the top surface of the metal plate, the dispensing tip having an open end configured to dispense liquid droplets and another end connected to the vessel, wherein there is a gap of at least 0.1 cm between the top surface of the metal plate and the open end of the dispensing tip;
    dispensing an aliquot of the liquid composition through the open end of the dispensing tip as a single droplet onto the top surface of the metal plate in a manner that maintains the droplet as a single droplet having a substantially spherical shape as it contacts and freezes on the top surface; and lyophilizing the frozen droplet to produce a dried pellet of substantially spherical shape.

12. The container of claim 11, wherein the lyophilized pellet has a reconstitution time of less than 3 minutes or less than 2 minutes or less than 1 minute.

13. The container of claim 11, wherein the container is a glass vial.

14. The container of claim 11, wherein the container comprises first and second compartments, with the at least one lyophilized pellet present in the first compartment and a reconstitution liquid present in the second compartment.

15. The container of claim 11, wherein the lyophilized pellet comprises a TNFRII-Fc fusion protein, and is prepared from a liquid composition comprising 25 mg/ml of a TNFRII-Fc fusion protein, 40 mg/ml mannitol, 10 mg/ml sucrose, and 1.2 mg/ml tromethamine in sterile water, pH 7.

16. A container comprising at least two dried pellets that are substantially spherical in shape, wherein one of the two dried pellets comprises a first biological material and the other dried pellet comprises a second biological material that is different than the first biological material, wherein each of the two dried pellets in the container is prepared by:
    providing a vessel which contains a liquid composition comprising the first and second biological materials;
    providing a metal plate which comprises a top surface that is solid and flat and does not contain a hydrophobic film and a bottom surface that is in physical contact with a heat sink adapted to maintain the top surface of the metal plate at a temperature of −90° C. or below;
    positioning a dispensing tip above the top surface of the metal plate, the dispensing tip having an open end configured to dispense liquid droplets and another end connected to the vessel, wherein there is a gap of at least 0.1 cm between the top surface of the metal plate and the open end of the dispensing tip;

dispensing an aliquot of the liquid composition through the open end of the dispensing tip as a single droplet onto the top surface of the metal plate in a manner that maintains the droplet as a single droplet having a substantially spherical shape as it contacts and freezes on the top surface; and lyophilizing the frozen droplet to produce a dried pellet of substantially spherical shape.

17. The container of claim 16, wherein each the first and second biological materials are components of a multi-component vaccine.

18. The method of claim 1, wherein the metal plate is selected from the group consisting of gold, silver, stainless steel, aluminum or copper.

19. The container of claim 11, wherein the metal plate is selected from the group consisting of gold, silver, stainless steel, aluminum or copper.

20. The container of claim 16, wherein the metal plate is selected from the group consisting of gold, silver, stainless steel, aluminum or copper.

* * * * *